United States Patent [19]
Kobzina

[11] 3,938,985
[45] Feb. 17, 1976

[54] SUBSTITUTED TRIAZINES

[75] Inventor: John W. Kobzina, Walnut Creek, Calif.

[73] Assignee: Chevron Research Company, San Francisco, Calif.

[22] Filed: Apr. 22, 1974

[21] Appl. No.: 462,905

Related U.S. Application Data

[63] Continuation-in-part of Ser. No. 288,245, Sept. 11, 1972, Pat. No. 3,819,626.

[52] U.S. Cl. .................................................. 71/93
[51] Int. Cl.² .......................................... A01N 9/22
[58] Field of Search ........................................ 71/93

[56] References Cited
UNITED STATES PATENTS

| | | | |
|---|---|---|---|
| 2,891,855 | 6/1959 | Gysin et al. | 71/93 |
| 3,261,835 | 7/1966 | Hamm et al. | 71/93 |
| 3,347,657 | 10/1967 | Knusli et al. | 71/93 |
| 3,595,639 | 7/1971 | Mason et al. | 71/93 |

FOREIGN PATENTS OR APPLICATIONS

| 109,004 | 3/1968 | Denmark | 71/93 |
|---|---|---|---|

*Primary Examiner*—Lewis Gotts
*Assistant Examiner*—Catherine L. Mills
*Attorney, Agent, or Firm*—G. F. Magdeburger; John Stoner, Jr.; Raymond Owyang

[57] ABSTRACT

Triazines of the formula

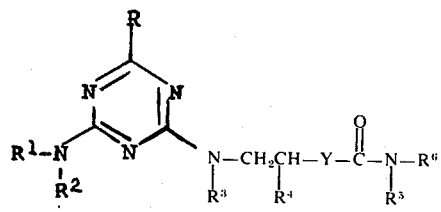

wherein R is chlorine, methoxy or methylthio, $R^1$ is alkyl, alkenyl or alkoxyalkyl; $R^2$, $R^3$, $R^4$ and $R^5$ are hydrogen or alkyl; $R^6$ is alkyl, aryl or haloaryl; and Y is oxygen or sulfur, are useful as herbicides.

20 Claims, No Drawings

SUBSTITUTED TRIAZINES

RELATED APPLICATION

This application is a continuation-in-part of application Ser. No. 288,245, filed Sept. 11, 1972, now U.S. Pat. No. 3,819,626, the disclosure of which is incorporated by reference.

BACKGROUND OF THE INVENTION

The present invention is directed to carbamyloxyalkylamino- and carbamylthioalkylamino-1,3,5-triazines and their use as herbicides.

Triazines and certain derivatives thereof are known to have utility in a variety of areas, such as fungicides and herbicides. For example, U.S. Pat. No. 2,891,855, issued June 23, 1959, to Gysin et al., and British Pat. No. 814,947, published June 17, 1959, disclose certain diamino-substituted 1,3,5-triazines and their use as herbicides.

DESCRIPTION OF THE INVENTION

The novel carbamyloxy- and carbamylthio-substituted triazines of the invention are represented by the formula

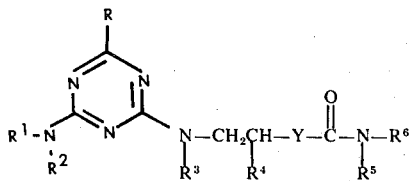

wherein R is chlorine, methoxy or methylthio; $R^1$ is alkyl of from 1 to 6 carbon atoms, alkenyl of 3 to 6 carbon atoms, or alkoxyalkyl of 2 to 6 carbon atoms; $R^2$, $R^3$, $R^4$ and $R^5$ are hydrogen or alkyl of 1 to 6 carbon atoms; $R^6$ is alkyl of 1 to 6 carbon atoms, monocarbocyclic aryl of 6 to 10 carbon atoms substituted with up to 3 (0 to 3) fluorine, chlorine or bromine atoms; and Y is oxygen or sulfur.

With reference to formula (I) and as used herein, the term "carbamyloxy" refers to the functional group

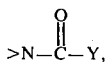

wherein Y is oxygen, and the term "carbamylthio" refers to the functional group

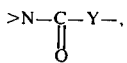

wherein Y is sulfur.

Representative alkyl groups which $R^1$, $R^2$, $R^3$, $R^4$, $R^5$ and $R^6$ may represent include methyl, ethyl, n-propyl, isopropyl, n-butyl, sec-butyl, t-butyl, n-pentyl, isohexyl, n-hexyl, etc.

Representative alkenyl groups which $R^1$ may represent include allyl, 2-butenyl, 2-pentenyl, 2-methyl-2-pentenyl, 3-hexenyl, etc.

Representative alkoxyalkyl groups which $R^1$ may represent include methoxymethyl, 2-methoxyethyl, 3-methoxypropyl, ethoxymethyl, 2-ethoxyethyl, 3-ethoxypropyl, butoxymethyl, etc.

Representative monocarbocyclic aryl groups which $R^6$ may represent include phenyl, alkylphenyl groups of 7 to 10 carbon atoms such as p-tolyl, o-tolyl, xylyl, 2,4-diethylphenyl, and o-isopropylphenyl; phenylalkyl groups of 7 to 10 carbon atoms such as benzyl, 2-phenylethyl and 3-o-tolylpropyl; halophenyl such as o-fluorophenyl, o,p-difluorophenyl, o-chlorophenyl, p-chlorophenyl, m,p-dichlorophenyl, o-bromophenyl, m-bromophenyl, m-bromo-p-chlorophenyl; and haloalkylphenyl and halophenylalkyl groups of 7 to 10 carbon atoms such as o-chloro-p-methylphenyl, o-fluoro-p-methylphenyl, o-methyl-p-chlorophenyl, m-chloro-m-methylphenyl; p-chlorobenzyl, o-fluorobenzyl and 3-(p-bromophenyl)propyl.

Preferred $R^1$ groups are alkyl and alkoxyalkyl groups, especially isopropyl and 3-methoxypropyl.

Preferred $R^2$, $R^3$, $R^4$, and $R^5$ groups are hydrogen and methyl. The particularly preferred $R^2$, $R^3$, $R^4$ and $R^5$ group is hydrogen.

Preferred $R^6$ groups are alkyl and phenyl substituted with 1 to 2 fluorine and chlorine atoms. Particularly preferred $R^6$ groups are alkyl of 1 to 3 carbon atoms, especially methyl.

Illustrative s-triazines of formula I wherein Y is sulfur include:

2-chloro-4-methylamino-6-(2-[methylcarbamylthio]-ethylamino)-s-triazine, 2-chloro-4-ethylamino-6-(2-[ethylcarbamylthio]-ethylamino)-s-triazine, 2-chloro-4-isopropylamino-6-(2-[methylcarbamylthio]-ethylamino)-s-triazine, 2-chloro-4-isopropylamino-6-(2-[ethylcarbamylthio]-ethylamino)-s-triazine, 2-chloro-4-isopropylamino-6-(2-[n-propylcarbamylthio]-ethylamino)-s-triazine, 2-chloro-4-isopropylamino-6-(2-[hexylcarbamylthio]-ethylamino)-s-triazine, 2-chloro-4-n-butylamino-6-(2-[methylcarbamylthio]-ethylamino)-s-triazine, 2-chloro-4-isopropylamino-6-(2-[methylcarbamylthio]-ethylamino)-s-triazine, 2-chloro-4-isopropylamino-6-(2-[dimethylcarbamylthio]-ethylamino)-s-triazine, 2-chloro-4-isopropylamino-6-(2-[diethylcarbamylthio]-ethylamino-s-triazine, 2-chloro-4-isopropylamino-6-(2-[phenylcarbamylthio]-ethylamino)-s-triazine, 2-chloro-4-isopropylamino-6-(2-[o-fluorophenylcarbamylthio]ethylamino)-s-triazine, 2chloro-4-propylamino-6-(2-[p-chlorophenylcarbamylthio]ethylamino)-s-triazine, 2-chloro-4-dimethylamino-6-(2-[p-tolylcarbamylthio]-ethylamino)-s-triazine, 2-chloro-4-diisopropylamino-6-(2-[o,p-difluorophenylcarbamylthio]ethylamino)-s-triazine, 2-chloro-4-isopropylamino-6-(-[benzylcarbamylthio]-ethylamino)-s-triazine, 2-chloro-4-methylethylamino-6-(2-[methylcarbamylthio]-ethylamino)-s-triazine, 2-chloro-4-allylamino-6-(2-[methylcarbamylthio]ethylamino-s-triazine, 2-chloro-4-(2-butenylamino)-6-(2-[methylcarbamylthio]-ethylamino)-s-triazine, 2-chloro-4-allylamino-6-(2-[o-chlorophenylcarbamylthio]-ethylamino)-s-triazine,
2-chloro-4-(methoxymethyl)amino-6-(2-[hexylcarbamylthio]-ethylamino)-s-triazine,
2chloro-4-(2-methoxyethylamino)-6-(2-[isopropylcarbamylthio]ethylamino)-s-triazine,
2-chloro-4-(3-methoxypropylamino)-6-(2-[methylcarbamylthio]ethylamino)-s-triazine,
2-chloro-4-(3-methoxypropylamino)-6-(2-[ethylcarbamylthio]-ethylamino)-s-triazine,
2-chloro-4-(3-methoxypropylamino)-6-(2-[phenylcarbamylthio]ethylamino)-s-triazine,
2-chloro-4-(3-methoxypropylamino)-6-[2-o-tolylcarbamylthio]ethylamino)-s-triazine,
2-chloro-4-(3-methoxypropylamino)-6-(2-[benzylcarbamylthio]ethylamino)-s-triazine,
2-methoxy-4-isopropylamino-6-(2-[methylcarbamylthio]-ethylamino)-s-triazine,
2-methoxy-4-isopropylamino-6-(2-[ethylcarbamylthio]ethylamino)-s-triazine,
2-methoxy-4-dimethylamino-6-(2-[m-chlorophenylcarbamylthio]ethylamino)-s-triazine,
2-methoxy-4-(methoxymethyl)amino-6-(2-[phenylcarbamylthio]-ethylamino)-s-triazine,
2-methoxy-4-(2-methoxypropylamino)-6-(2-[methylcarbamylthio]ethylamino)-s-triazine,
2-methoxy-4-allylamino-6-(2-[methylcarbamylthio]ethylamino)-s-triazine,
2-methoxy-4-(methoxymethyl)isopropylamino-6-(2-[methylcarbamylthio]ethylamino)-s-triazine,
2-methoxy-4-isobutylamino-6-(2-[methylcarbamylthio]ethylamino)-s-triazine,
2-methoxy-4-hexylamino-6-(2-[dimethylcarbamylthio]ethylamino)-s-triazine, -s-triazine,
2-methoxy-4-isopropylamino-6-(2-[benzylcarbamylthio]ethylamino)-s-triazine,
2-methylthio-4-isopropylamino-6-(2-[methylcarbamylthio]ethylamino-s-triazine,
2-methylthio-4-allylamino-6-(2-[ethylcarbamylthio]ethylamino-s-triazine,
2-methylthio-4-(methoxymethyl)amino-6-(2-[phenylcarbamylthio]ethylamino)-s-triazine,
2-methylthio-4-dimethylamino-6-(2-[o-fluorophenylcarbamylthio]ethylamino-s-triazine,
2-methylthio-4-allylmethylamino-6-(2-[methylcarbamylthio]ethylamino-s-triazine,
2-methylthio-4-isopropylamino-6-(2-[dimethylcarbamylthio]ethylamino)-s-triazine,
2-chloro-4-isopropylamino-6-(2-[methylcarbamylthio]propylamino)-s-triazine,
2-methoxy-4-isopropylamino-6-(2-[methylcarbamylthio]propylamino)-s-triazine,
2-methylthio-4-isopropylamino-6-(2-[phenylcarbamylthio]propylamino)-s-triazine,
2-chloro-4-allylamino-6-(2-[o-bromophenylcarbamylthio]-propylamino)-s-triazine,
2-chloro-4-ethylamino-6-(2-[benzylcarbamylthio]-propylamino)-s-triazine,
2-chloro-4-isopropylamino-6-{N-methyl-N-(2-[methylcarbamylthio]ethyl)amino}-s-triazine,
2-methoxy-4-allylamino-6-{N-methyl-N-(2-[o-chlorophenylcarbamylthio]ethyl)amino}-s-triazine,
2-methylthio-4-(methoxymethyl)amino-6-{N-methyl-N-(2-[dimethylcarbamylthio]ethyl)amino}-s-triazine, and
2-methylthio-4-isopropylamino-6-{(N-methyl-N-(2-[p-chlorobenzylcarbamylthio]ethyl)amino}-s-triazine.

Illustrative s-triazines of formula (I) wherein Y is oxygen include:
2-chloro-4-methylamino-6-(2-[methylcarbamyloxy]ethylamino)-s-triazine,
2-chloro-4-ethylamino-6-(2-[ethylcarbamyloxy]ethylamino)-s-triazine,
2-chloro-4-isopropylamino-6-(2-[methylcarbamyloxy]ethylamino)-s-triazine,
2-chloro-4-isopropylamino-6-(2-[ethylcarbamyloxy]ethylamino-s-triazine,
2-chloro-4-isopropylamino-6-(2-[n-propylcarbamyloxy]ethylamino)-s-triazine,
2-chloro-4-isopropylamino-6-(2-[hexylcarbamyloxy]ethylamino-s-triazine,
2-chloro-4-n-butylamino-6-(2-[methylcarbamyloxy]ethylamino-s-triazine,
2-chloro-4-isopropylamino-6-(2-[methylcarbamyloxy]ethylamino)-s-triazine,
2-chloro-4-isopropylamino-6-(2-[dimethylcarbamyloxy]ethylamino)-s-triazine,
2-chloro-4-isopropylamino-6-(2-[diethylcarbamyloxy]ethylamino)-s-triazine,
2-chloro-4-isopropylamino-6-(2-[phenylcarbamyloxy]ethylamino)-s-triazine,
2-chloro-4-isopropylamino-6-(2-[o-fluorophenylcarbamyloxy]ethylamino-s-triazine,
2-chloro--4-propylamino-6-(2-[p-chlorophenylcarbamyloxy]ethylamino)-s-triazine,
2-chloro-4-dimethylamino-6-(2-[p-tolylcarbamyloxy]ethylamino)-s-triazine,
2-chloro-4-diisopropylamino-6-(2-[o.p-difluorophenylcarbamyloxy]ethylamino)-s-triazine,
2-chloro-4-isopropylamino-6-(2-[benzylcarbamyloxy]ethylamino-s-triazine,
2-chloro-4-methylethylamino-6-(2-[methylcarbamyloxy]ethylamino)-s-triazine,
2-chloro-4-allylamino-6-(2-[methylcarbamyloxy]ethylamino-s-triazine,
2-chloro-4-(2-butenylamino)-6-(2-[methylcarbamyloxy]ethylamino)-s-triazine,
2-chloro-4-allylamino-6-(2-[o-chlorophenylcarbamyloxy]ethylamino)-s-triazine,
2-chloro-4-(methoxymethyl)amino-6-(2-[hexylcarbamyloxy]ethylamino)-s-triazine,
2-chloro-4-(2-methoxyethylamino)-6-(2-[isopropylcarbamyloxy]ethylamino)-s-triazine,
2-chloro-4-(3-methoxypropylamino)-6-(2-[methylcarbamyloxy]ethylamino)-s-triazine,
2-chloro-4-(3-methoxypropylamino)-6-(2-[ethylcarbamyloxy]ethylamino)-s-triazine,
2-chloro-4-(3-methoxypropylamino)-6-(2-[phenylcarbamyloxy]ethylamino)-s-triazine,
2-chloro-4-(3-methoxypropylamino)-6-[2-o-tolylcarbamyloxy]ethylamino)-s-triazine, 2-chloro-4-(3 methoxypropylamino)-6-(2-[benzylcarbamyloxy]ethylamino)-s-triazine,
2-methoxy-4-isopropylamino-6-(2-[methylcarbamyloxy]ethylamino-s-triazine,
2-methoxy-4-isopropylamino-6-(2-[ethylcarbamyloxy]ethylamino)-s-triazine,
2-methoxy-4-dimethylamino-6-(2-[m-chlorophenylcarbamyloxy]ethylamino-s-triazine,
2-methoxy-4-(methoxymethyl)amino-6-(2-[phenylcarbamyloxy]ethylamino)-s-triazine,
2-methoxy-4-(2-methoxypropylamino)-6-(2-[methylcarbamyloxy]ethylamino)-s-triazine, 2-methoxy-4-allylamino-6-(2-[methylcarbamyloxy]ethylamino)-s-triazine,
2-methoxy-4-(methoxymethyl)isopropylamino-6-(2-[methylcarbamyloxy]ethylamino)-s-triazine,
2-methoxy-4-isobutylamino-6-(2-[methylcarbamyloxy]ethylamino-s-triazine,
2-methoxy-4-hexylamino-6-(2-[dimethylcarbamyloxy]ethylamino)-s-triazine,
2-methoxy-4-isopropylamino-6-(2-[benzylcarbamyloxy]ethylamino)-s-triazine,
2-methylthio-4-isopropylamino-6-(2-[methylcarbamyloxy]ethylamino)-s-triazine,
2-methylthio-4-allylamino-6-(2-[ethylcarbamyloxy]ethylamino-s-triazine,
2-methylthio-4-(methoxymethyl)amino-6-(2-[phenylcarbamyloxy]ethylamino)-s-triazine,
2-methylthio-4-dimethylamino-6-(2-[o-fluorophenylcarbamyloxy]ethylamino-s-triazine,
2-methylthio-4-allylmethylamino-6-(2-[methylcarbamyloxy]ethylamino)-s-triazine,
2-methylthio-4-isopropylamino-6-(2-[dimethylcarbamyloxy]ethylamino)-s-triazine,
2-chloro-4-isopropylamino-6-(2-[methylcarbamyloxy]propylamino-s-triazine,
2-methoxy-4-isopropylamino-6-(2-[methylcarbamyloxy]propylamino)-s-triazine,
2-methylthio-4-isopropylamino-6-(2-[phenylcarbamyloxy]propylamino)-s-triazine,
2-chloro-4-allylamino-6-(2-[o-bromophenylcarbamyloxy]propylamino-s-triazine,
2-chloro-4-ethylamino-6-(2-[benzylcarbamyloxy]propylamino-s-triazine,
2-chloro-4-isopropylamino-6-{N-methyl-N-(2-[methylcarbamyloxy]ethyl)amino}-s-triazine,
2-methoxy-4-allylamino-6-{N-methyl-N-(2-[o-chlorophenylcarbamyloxy]ethyl)amino}-s-triazine,
2-methylthio-4-(methoxymethyl)amino-6-{N-methyl-N-(2-[dimethylcarbamyloxy]ethyl)amino}-s-triazine, and
2-methylthio-4-isopropylamino-6-{N-methyl-N-(2-[p-chlorobenzylcarbamyloxy]ethyl)amino}-s-triazine.

The preferred triazines of the invention are those wherein Y is sulfur, R is chloro, $R^1$ is isopropyl or 3-methoxypropyl, $R^6$ is methyl and $R^2$, $R^3$, $R^4$ and $R^5$ are hydrogen.

The compounds of the invention may be prepared by the reaction of a chloro-s-triazine (III) and a carbamyloxy- or carbamylthio-substituted amine (II), according to the following equation (1)

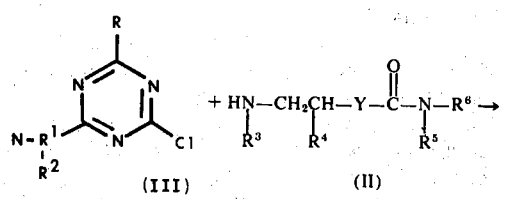

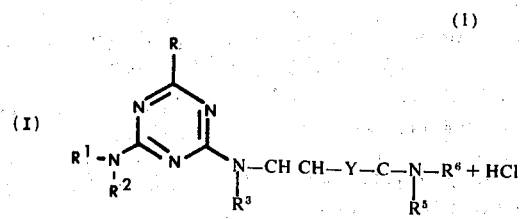

(1)

wherein R, $R^1$, $R^2$, $R^3$, $R^4$, $R^5$, $R^6$ and Y have the same significance as previously defined. This reaction is conducted by contacting substantially equimolar amounts of the chloro-s-triazine (III) and the amine (II) in an inert solvent, e.g., chlorobenzene, at 25°C. to 100°C. A strong base, e.g., sodium hydroxide, is employed to neutralize the hydrochloric acid formed in the reaction and to maintain the reaction medium neutral or slightly basic, e.g., pH 7–9.

In a modification of the reaction, the hydrochloride salt of the amine (II) is provided to the reaction mixture and the free amine (II) is generated by the addition of an equimolar amount of a strong inorganic base, e.g., sodium hydroxide. The product is isolated by conventional procedures, e.g., filtration, extraction, chromatography, etc.

The hydrochloride salt of the amine (II) is prepared by conventional procedures from a hydroxy- or mercapto-amine hydrochloride (IV) and a carbamyl chloride (V), according to the following equation (2)

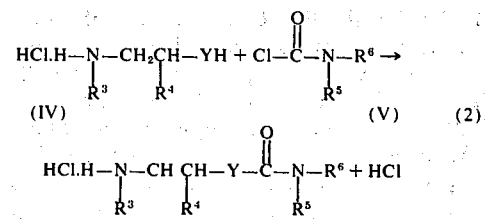

(2)

The hydrochloride salt is then converted to the amine (II).

Alternatively, the compounds of the invention may be prepared by the reaction of a carbamyl chloride (V) and a hydroxy- or mercapto-alkylamino-s-triazine (VI), according to the following equation (3)

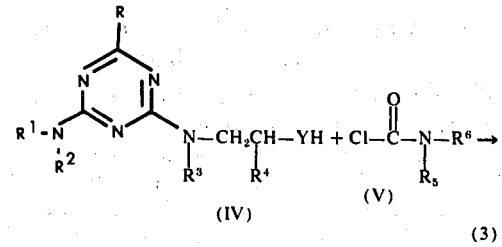

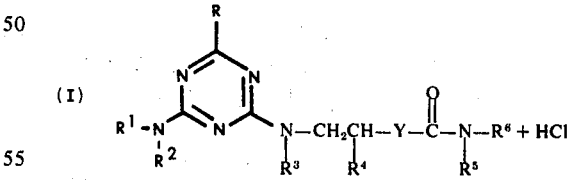

(3)

wherein R, $R^1$, $R^2$, $R^3$, $R^4$, $R^5$, $R^6$ and Y have the same significance as previously defined. This reaction is conducted by contacting substantially equimolar amounts of the triazine (VI) and the carbamyl chloride (V) in the presence of a base, e.g., inorganic bases such as sodium methoxide or organic bases such as triethylamine or pyridine, in an inert solvent at a temperature of 25°C. to 100°C. The product is then isolated by conventional procedures, e.g., extraction, filtration, chromatography, etc.

The compounds of the invention wherein $R^5$ is hydrogen may also be prepared by the reaction of an isocyanate (VII) and a hydroxy- or mercapto-alkylamino-s-triazine (VI), according to the following equation (4)

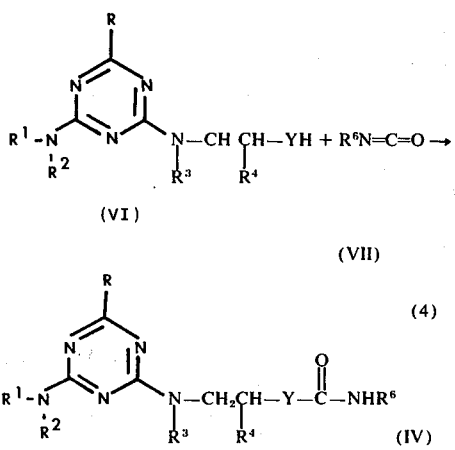

wherein R, $R^1$, $R^2$, $R^3$, $R^4$, $R^6$ and Y have the same significance as previously described. This reaction is conducted by conventional procedures. Generally, equimolar amounts of the triazine (VI) and the isocyanate (VII) are used. A small amount of an organic base, e.g., triethylamine, may be employed as a catalyst. The reaction is generally conducted in the presence of an inert solvent, e.g., dimethoxyethane, methylene dichloride or benzene. The reaction temperature suitably ranges from 0°C. to 100°C. and the reaction time from one-half to 72 hours. The crude product may be purified by recrystallization or chromatography.

The preparation of the triazines of the invention is exemplified by the following examples.

EXAMPLES

Example 1 —
2-Chloro-4-Isopropylamino-6-(2-[Methylcarbamylthio]ethylamino)-s-Triazine A solution of 5 g of 2-chloro-4-isopropylamino-6-(2-mercaptoethylamino)-2-triazine, 1.38 g methyl isocyanate and 10 drops triethylamine in 20 ml benzene was heated at 100°C. for 2 hours and then allowed to cool overnight. The product was filtered and dried. The melting point and elemental analysis are tabulated in Table I.

Example 2 —
2-Chloro-4-(3-Methoxypropylamino)-6-(2-[Methylcarbamyloxy]ethylamino)-s-Triazine A solution of 5 g 2-chloro-4-(3-methoxypropylamino)-6-(2-hydroxyethylamino)-s-triazine, 1.2 g methyl isocyanate and 10 drops triethylamine in 20 ml dimethylformamide was heated at 100°C. for 2 hours. The dimethylformamide was removed by distillation and the resulting residue was slurried with ether and filtered to give the product as a white powder. The melting point and elemental analysis on the product are tabulated in Table I.

EXAMPLE 3 —
2-Methoxy-4-Isopropylamino-6-(2-[o-Fluorophenylcarbamyloxy]ethylamino)-s-Triazine A solution of 5 g of 2-methoxy-4-isopropylamino-6-(2-hydroxyethylamino)-s-triazine, 3.0 g o-fluorophenyl isocyanate and 10 drops triethylamine was stirred at 25°C. for about 2 days. The reaction mixture was filtered to give the product. The melting point and elemental analysis on the product are tabulated in Table I.

Example 4 —
2-Chloro-4-Ethylamino-6-(2-[methylcarbamylthio]ethylamino)-s-Triazine A solution of 2.25 g ethylamine in 5 ml water was mixed with a solution of 9.22 g cyanuric chloride in 80 ml chlorobenzene at about 0°C. A solution of 2 g sodium hydroxide in 5 ml water was added and the reaction mixture stirred at 0°C. for 1.5 hours.

To the unisolated 2,6-dichloro-4-ethylamino-s-triazine, prepared above, was added a solution of 8.53 g 2-(methylcarbamylthio)ethylamine hydrochloride in 15 ml water followed by a solution of 2 g sodium hydroxide in 5 ml of water. The reaction mixture was then warmed to 50°C. and an additional 2 g sodium hydroxide in 5 ml water was added dropwise at a rate sufficient to maintain the reaction slightly basic. After the addition was completed, the reaction mixture was stirred at 50°C. for 0.5 hour. The crude product was isolated by filtration, slurried with warm water and filtered, and dried. The melting point and elemental analysis of the product are tabulated in Table I.

Example 5 —
2-Chloro-4-Isopropylamino-6-(2-Mercaptoethylamino)-s-Triazine

A solution of 5.91 g isopropylamine in 6 ml water was added dropwise to 18.44 g cyanuric chloride in 80 ml chlorobenzene at 0° to −5°C. A solution of 4 g sodium hydroxide in 10 ml water was added and the reaction mixture stirred at 0°C. for 1 hour.

To the unisolated 2,6-dichloro-4-isopropylamino-s-triazine, prepared above, was added a solution of 11.36 g 2-mercaptoethylamine hydrochloride in 30 ml water followed by a solution of 4 g sodium hydroxide in 10 ml water. The reaction mixture was then warmed to 50°C. and an additional 4 g sodium hydroxide in 10 ml water was added. The reaction mixture (slightly basic) was stirred at 50°C. for 0.5 hour and at about 25°C. overnight. The chlorobenzene layer was separated. The aqueous layer was extracted with benzene. The combined organic solutions were dried over magnesium sulfate and evaporated under reduced pressure to give the crude product. Recrystallization from ether gave the product as a white solid, m.p. 141°–146°C. Elemental analysis showed: %S, calc. 12.9, found 12.7; %Cl, calc. 14.3, found 14.7.

The product is an example of a mercapto-alkylamine-s-triazine represented by formula (VI) wherein Y is sulfur. In addition to being intermediates for the preparation of the compounds of the invention, these novel mercapto-alkylamino-s-triazines are useful as herbicides. The herbicidal activity of the product of this example is provided in Table II identified by an *.

Example 6 —
2-Chloro-4-Isopropylamino-6-(2-[Dimethylcarbamylthio]ethylamino)-s-Triazine A 0.46-g sample of sodium was added to 50 ml methanol in small pieces. To the resulting sodium methoxide solution was added 5 g of 2-chloro-4-isopropylamino-6-(2-mercaptoethylamino)-s-triazine, followed by 2.16 g dimethylcarbamyl chloride at 0°C. The reaction mixture was heated at 80°C. for 4 hours, cooled, filtered and evaporated under reduced pressure to give a yellow oil. The yellow oil was dissolved in 1:1 ether/acetone and filtered. The filtrate was evaporated to give the product as an oil. The elemental analysis on the product is tabulated in Table I.

Other compounds of the invention were prepared by the procedures of Examples 1-6 and are tabulated in Table I.

UTILITY

The triazines of the present invention are, in general, herbicidal in both pre- and post-emergent applications. For pre-emergent control of undesirable vegetation, these triazines will be applied in herbicidal quantities to the growth environment, e.g., soil infested with seeds and/or seedlings of such vegetation. Such application will inhibit the growth of or kill the seeds, germinating seeds and seedlings. For post-emergent applications the triazines of the present invention will be applied directly to the foliage and other plant parts. Generally they are effective against weed grasses as well as broad-leaved weeds. Some may be selective with respect to type of application and/or type of weed.

Pre- and post-emergent herbicidal tests on representative triazines of this invention were made using the following methods:

Pre-Emergent Test

An acetone solution of the test triazines was prepared by mixing 750 mg triazine, 220 mg of a nonionic surfactant and 25 ml of acetone. This solution was added to approximately 125 ml of water containing 156 mg of surfactant.

Seeds of the test vegetation were planted in a pot of soil and the triazine solution was sprayed uniformly onto the soil surface at a dose of 100 mcg/cm². The pot was watered and placed in a greenhouse at a temperature of about 80°-85°F. The pot was watered intermittently and was observed for seedling emergence, health of emerging seedlings, etc., for a 3-week period. At the end of this period, the herbicidal effectiveness of the triazine was rated based on the physiological observations. A 0-to-100 scale was used, 0 representing no phytotoxicity and 100 representing complete kill.

Post-Emergent Test

The test triazine was formulated in the same manner as described for the pre-emergent test. The concentration of the triazine in this formulation was 5,000 ppm. This formulation was uniformly sprayed on the pot containing 24-day-old plants (approximately 15 to 25 plants per pot) at a dose of 100 mcg/cm². The pots were then placed in a greenhouse at a temperature of 80°-85°F. and then watered intermittently at their base as needed. The plants were observed periodically for phytotoxic effects and physiological and morphological responses to the treatment. After 3 weeks, the herbicidal effectiveness of the triazine was rated based on these observations. A 0-to-100 scale was used, 0 representing no phytotoxicity, 100 representing complete kill.

The amount of the triazine administered will vary with the particular plant part or plant growth medium which is to be contacted, the general location of application, i.e., sheltered areas such as greenhouses as compared to exposed areas such as fields, as well as the desired type of control. For pre-emergent control of most plants, dosages in the range of about 0.5 to 20 lbs/acre will be used. Such administration will give a concentration of about 2 to 80 ppm triazine distributed throughout 0.1 acre-foot. For post-emergent application, such as foliar spray application, compositions containing about 0.5 to 8 lbs. triazine per 100 gal. spray will be used. Such application is equivalent to about 0.5 to 20 lbs triazine per acre.

The herbicidal compositions of this invention comprise an herbicidal amount of one or more of the above-described triazines intimatedly admixed with a biologically inert carrier. The carrier may be a liquid diluent such as water or acetone, or a solid. The solid may be in the form of dust powder or granules. These compositions will also usually contain adjuvants such as a wetting or dispersing agent to facilitate their penetration into the plant growth medium or plant tissue and generally enhance their effectiveness. These compositions may also contain other pesticides, stabilizers, conditioners, fillers and the like.

The triazines of the invention are also useful for the control of bacteria and fungi. For example, 2-chloro-4-diethylamino-6-(2-propylcarbamoylthioethylamino)-s-triazine and 2-chloro-4-allylamino-6-(2-propylcarbamoylthioethylamino)-s-triazine have been found to be effective for the control of *Botrytis cinerea*.

TABLE I

PHYSICAL PROPERTIES AND ELEMENTAL ANALYSIS FOR COMPOUNDS OF THE FORMULA

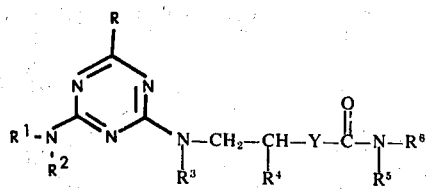

| No. | R | R¹ | R² | R³ | R⁴ | R⁵ | R⁶ | Y | Melting Point, °C. | Nitrogen Calc. | Nitrogen Found | Chlorine Calc. | Chlorine Found |
|---|---|---|---|---|---|---|---|---|---|---|---|---|---|
| 1 | CH₃O | C₂H₅ | H | H | H | H | CH₃ | O | — | 31.1 | 29.1 | | |
| 2 | Cl | CH₃ | CH₃ | H | H | H | CH₃ | O | 162-164 | 30.6 | 30.0 | 12.9 | 12.7 |
| 3 | Cl | CH₃ | CH₃ | H | H | H | φ* | O | 178-181 | 25.0 | 23.6 | 10.5 | 10.5 |
| 4 | Cl | CH₃ | CH₃ | H | H | H | p-Cl-φ | O | 201-204 | 22.6 | 21.0 | 19.1 | 19.5 |
| 5 | Cl | CH₃ | CH₃ | H | H | H | o-F-φ | O | 167-170 | 23.7 | 23.8 | 10.0 | 9.9 |
| 6 | CH₃O | C₂H₅ | H | H | H | H | φ | O | 122-124 | 25.3 | 25.7 | | |
| 7 | CH₃O | C₂H₅ | H | H | H | H | p-Cl-φ | O | 137-139 | 22.9 | 23.1 | | |
| 8 | CH₃O | C₂H₅ | H | H | H | H | o-F-φ | O | 118-120 | 24.0 | 23.9 | | |
| 9 | Cl | C₂H₅ | H | H | H | H | φ | O | 190-194 | 25 | 24.7 | | |

TABLE I-continued

PHYSICAL PROPERTIES AND ELEMENTAL ANALYSIS FOR COMPOUNDS OF THE FORMULA

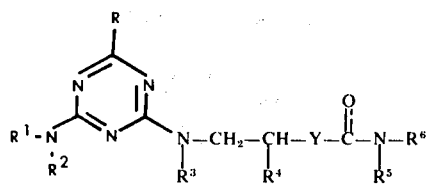

| No. | R | R¹ | R² | R³ | R⁴ | R⁵ | R⁶ | Y | Melting Point, °C. | Nitrogen Calc. | Nitrogen Found | Chlorine Calc. | Chlorine Found |
|---|---|---|---|---|---|---|---|---|---|---|---|---|---|
| 10 | Cl | C₂H₅ | H | H | H | H | p-Cl-φ | O | 200–204 | | | 19.1 | 19.3 |
| 11 | Cl | C₂H₅ | H | H | H | H | CH₃ | O | 181–184 | 30.6 | 29.8 | | |
| 12 | Cl | C₂H₅ | H | H | H | H | o-F-φ | O | 185–188 | 23.7 | 23.8 | | |
| 13 | CH₃O | (CH₃)₂CH | H | H | H | H | φ | O | 70–73 | 24.3 | 22.4 | | |
| 14 | CH₃O | C₂H₅ | H | H | H | H | CH₃ | O | oil | 27.4 | 26.8 | | |
| 15 | CH₃O | (CH₃)₂CH | H | H | H | H | CH₃ | O | oil | 29.6 | 28.7 | | |
| 16 | CH₃O | (CH₃)₂CH | H | H | H | H | p-Cl-φ | O | 107–108 | | | 9.3 | 9.6 |
| 17 | CH₃O | (CH₃)₂CH | H | H | H | H | o-F-φ | O | 68–70 | 23.1 | 20.8 | | |
| 18 | Cl | (CH₃)₂CH | H | H | H | H | CH₃ | S | 141–144 | | | 11.6 | 11.7 |
| 19 | Cl | (CH₃)₂CH | H | H | H | H | p-Cl-φ | S | 130–132 | | | 17.7 | 18.8 |
| 20 | Cl | (CH₃)₂CH | H | H | CH₃ | H | p-Cl-φ | O | 191–193 | | | 17.8 | 17.8 |
| 21 | Cl | (CH₃)₂CH | H | H | CH₃ | H | CH₃ | O | 114–116 | | | 11.7 | 11.5 |
| 22 | CH₃O | (CH₃)₂CH | H | H | CH₃ | H | p-Cl-φ | O | 50–55 | | | 9.0 | 9.1 |
| 23 | CH₃O | (CH₃)₂CH | H | H | CH₃ | H | CH₃ | O | 57–63 | 28.2 | 24.6 | | |
| 24 | Cl | (CH₃)₂CH | H | CH₃ | H | H | p-Cl-φ | O | 45–50 | | | 17.8 | 17.7 |
| 25 | Cl | (CH₃)₂CH | H | CH₃ | H | H | CH₃ | O | 105–110 | | | 11.7 | 11.9 |
| 26 | CH₃O | (CH₃)₂CH | H | CH₃ | H | H | CH₃ | O | oil | 28.2 | 25.6 | | |
| 27 | Cl | (CH₃)₂CH | H | CH₃ | H | H | p-Cl-φ | O | — | | | 9.0 | 8.4 |
| 28 | Cl | CH₃O(CH₂)₃ | H | H | H | H | CH₃ | O | 155–158 | | | 11.1 | 10.5 |
| 29 | Cl | CH₃O(CH₂)₂ | H | H | H | H | CH₃ | O | 154–158 | | | 11.6 | 12.3 |
| 30 | Cl | CH₂=CHCH₂ | H | H | H | H | CH₃ | O | 163–170 | | | 12.4 | 11.3 |
| 31 | Cl | C₂H₅ | H | H | H | H | CH₃CH₂CH₂ | S | 182–187 | | | 12.2 | 12.6 |
| 32 | Cl | CH₃CH₂ | CH₃CH₂ | H | H | H | CH₃CH₂CH₂ | S | 139–141 | | | 11.1 | 10.9 |
| 33 | Cl | CH₂=CHCH₂ | H | H | H | H | CH₃CH₂CH₂ | S | 189–203 | | | 11.7 | 11.2 |
| 34 | Cl | CH₃O(CH₂)₃ | H | H | H | H | CH₃CH₂CH₂ | S | 154–156 | | | 10.6 | 10.7 |
| 35 | Cl | CH₃(CH₂)₃ | H | H | H | H | CH₃ | S | 181–184 | | | 11.1 | 11.4 |
| 36 | Cl | CH₃OCH₂ | CH₃ | H | H | H | CH₃ | S | oil | | | 10.6 | 11.2 |
| 37 | Cl | (CH₃)₂CH | CH₃ | H | H | H | CH₃CH₂CH₂ | S | 113–115 | | | 10.7 | 10.7 |
| 38 | Cl | (CH₃)₂CH | H | H | H | H | φ | S | 126–130 | | | 9.7 | 9.5 |
| 39 | Cl | CH₃O(CH₂)₃ | H | H | H | H | φ | S | 161–166 | | | 8.9 | 8.9 |
| 40 | Cl | C₂H₅ | H | H | H | H | CH₃ | S | 163–168 | | | 12.2 | 12.4 |
| 41 | Cl | C₂H₅ | C₂H₅ | H | H | H | CH₃ | S | 165–170 | | | 11.1 | 11.0 |
| 42 | Cl | CH₂=CHCH₂ | H | H | H | H | CH₃ | S | 192–195 | | | 11.7 | 12.9 |
| 43 | Cl | CH₃O(CH₂)₃ | H | H | H | H | CH₃ | S | 138–145 | | | 10.6 | 11.5 |
| 44 | Cl | CH₃(CH₂)₃ | H | H | H | H | CH₃ | S | 171–174 | | | 11.1 | 12.6 |
| 45 | Cl | (CH₃)₂CH | H | H | H | CH₃ | CH₃ | S | — | | | 11.1 | 11.1 |
| 46 | Cl | (CH₃)₂CH | C₂H₅ | H | H | (CH₃)₂CH | (CH₃)₂CH | S | oil | | | 9.5 | 9.0 |

*represents phenyl

TABLE II

HERBICIDAL ACTIVITY FOR COMPOUNDS OF TABLE I

| | Herbicidal Effectiveness Pre/Post | | | | | |
|---|---|---|---|---|---|---|
| No. | O | W | C | M | P | L |
| 1 | 100/100 | 95/100 | 100/95 | 100/100 | 100/100 | 100/100 |
| 2 | 30/10 | 30/10 | 45/10 | 90/80 | 95/55 | 95/55 |
| 3 | 20/ | 10/ | 20/ | 30/ | 85/15 | 75/20 |
| 4 | 20/ | | | /20 | 25/45 | /75 |
| 5 | /10 | /10 | /10 | /10 | /10 | |
| 6 | 90/65 | 90/75 | 100/70 | 95/100 | 100/100 | 100/100 |
| 7 | 80/85 | /80 | 25/80 | 65/100 | 75/100 | 100/100 |
| 8 | 55/80 | 75/95 | 90/95 | 100/100 | 100/100 | 100/100 |
| 9 | | | | 10/10 | 15/10 | 75/10 |
| 10 | 20/30 | 10/15 | 20/30 | 45/55 | 60/60 | 100/85 |
| 11 | 73/ | 80/10 | 98/10 | 99/64 | 100/88 | 100/97 |
| 12 | /25 | | | 15/ | | /25 |
| 13 | 10/100 | 25/65 | 40/73 | 98/100 | 95/100 | 100/100 |
| 14 | 35/25 | 30/25 | 20/30 | 95/100 | 75/85 | 85/100 |
| 15 | 100/94 | 95/75 | 100/65 | 100/100 | 100/100 | 100/100 |
| 16 | 70/40 | 15/35 | 50/35 | 95/95 | 95/100 | 95/100 |
| 17 | 30/75 | 55/50 | 90/65 | 95/100 | 95/95 | 100/100 |
| * | 100/100 | 70/75 | 75/ | 100/100 | 100/100 | 100/100 |
| 18 | 95/95 | 90/75 | 90/60 | 100/100 | 100/100 | 100/100 |
| 19 | | | | | /25 | |
| 20 | /10 | /10 | /10 | /50 | /50 | 30/40 |
| 21 | 10/20 | 35/ | | 80/80 | 55/40 | 55/50 |
| 22 | 25/65 | 20/25 | 45/ | 95/100 | 65/75 | 85/85 |
| 23 | 90/45 | 80/10 | 100/ | 95/50 | 100/55 | 100/75 |
| 24 | 20/30 | /25 | /15 | 90/100 | 100/90 | 100/95 |
| 25 | 55/10 | 75/ | 55/ | 100/65 | 100/60 | 100/70 |
| 26 | | | 15/ | 15/25 | 30/60 | |
| 27 | /90 | /50 | /25 | 15/95 | 90/90 | 90/100 |
| 28 | 100/10 | 30/ | 100/ | 100/100 | 100/80 | 100/70 |

TABLE II-continued
HERBICIDAL ACTIVITY FOR COMPOUNDS OF TABLE I

| No. | Herbicidal Effectiveness Pre/Post | | | | | |
|---|---|---|---|---|---|---|
|  | O | W | C | M | P | L |
| 29 | 70/ | 10/ | 40/ | 95/ | 50/25 | 95/30 |
| 30 |  |  |  | 35/20 |  |  |
| 31 |  |  |  |  |  | 60/ |
| 34 | 35/ | 25/ | 70/ | 85/15 | /15 | 95/15 |
| 35 | /15 |  |  |  |  |  |
| 36 | 40/20 |  |  | 65/40 | 15/40 | 90/45 |
| 37 | 20/ | 10/ |  | 80/50 | 55/ | 90/10 |
| 38 | 50/20 | 20/ |  | 74/80 | 55/55 | 90/75 |
| 39 |  |  |  | 50/ | 25/ | 50/ |
| 40 | 95/35 | 85/ | 85/ | 100/85 | 100/70 | 100/70 |
| 43 |  |  |  | /65 |  |  |
| 44 |  |  |  | 80/93 | /25 | /65 |
| 45 | 20/65 | 20/10 | /10 | 95/100 | 65/100 | 95/100 |

*2-Chloro-4-isopropylamino-6-(2-mercaptoethylamino)-s-triazine
O = Wild Oats (*Avena fatua*)
W = Watergrass (*Echinochloa crusgalli*)
C = Crabgrass (*Digitaria sanguinalis*)
M = Mustard (*Brassica arvensis*)
P = Pigweed (*Amaranthus retroflexus*)
L = Lambsquarter (*Chenopodium album*)

What is claimed is:

1. A method for controlling the growth of undesirable vegetation which comprises applying to said vegetation an herbicidally effective amount of a compound of the formula

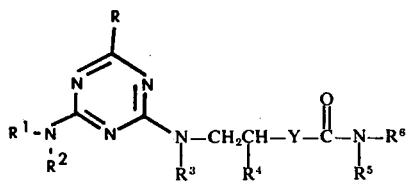

wherein R is chlorine, methoxy or methylthio; $R^1$ is alkyl of from 1 to 6 carbon atoms, alkenyl of 3 to 6 carbon atoms, or alkoxyalkyl of 2 to 6 carbon atoms; $R^2$, $R^3$, $R^4$ and $R^5$ are hydrogen or alkyl of 1 to 6 carbon atoms; $R^6$ is alkyl of 1 to 6 carbon atoms, monocarbocyclic aryl of 6 to 10 carbon atoms substituted with up to 3 (0 to 3) fluorine, chlorine or bromine atoms; and Y is oxygen or sulfur.

2. The method of claim 1 wherein $R^2$, $R^3$, $R^4$ and $R^5$ are hydrogen.
3. The method of claim 2 wherein $R^1$ is alkyl.
4. The method of claim 2 wherein $R^1$ is alkoxyalkyl.
5. The method of claim 2 wherein $R^6$ is alkyl.
6. The method of claim 2 wherein R is chlorine, Y is sulfur, $R^1$ is alkyl or alkoxyalkyl and $R^6$ is alkyl.
7. The method of claim 6 wherein $R^1$ is isopropyl and $R^6$ is methyl.
8. The method of claim 6 wherein $R^1$ is 3-methoxypropyl and $R^6$ is methyl.
9. The method of claim 2 wherein $R^6$ is phenyl substituted with 1 to 2 fluorine or chlorine atoms.

10. A composition comprising an herbicidally effective amount of the compound of claim 1 admixed with a biologically inert carrier.
11. A composition comprising an herbicidally effective amount of the compound of claim 2 admixed with a biologically inert carrier.
12. A composition comprising an herbicidally effective amount of the compound of claim 3 admixed with a biologically inert carrier.
13. A composition comprising an herbicidally effective amount of the compound of claim 4 admixed with a biologically inert carrier.
14. A composition comprising an herbicidally effective amount of the compound of claim 5 admixed with a biologically inert carrier.
15. A composition comprising an herbicidally effective amount of the compound of claim 6 admixed with a biologically inert carrier.
16. A composition comprising an herbicidally effective amount of the compound of claim 7 admixed with a biologically inert carrier.
17. A composition comprising an herbicidally effective amount of the compound of claim 8 admixed with a biologically inert carrier.
18. A composition comprising an herbicidally effective amount of the compound of claim 9 admixed with a biologically inert carrier.
19. The method of claim 1 wherein the compound is applied pre-emergently.
20. The method of claim 1 wherein the compound is applied post-emergently.

* * * * *